(12) United States Patent
Smith

(10) Patent No.: US 6,328,627 B1
(45) Date of Patent: *Dec. 11, 2001

(54) FOUNDATION GARMENT FOR THE RELIEF OF MENSTRUAL DISCOMFORT

(76) Inventor: R. Scott Smith, 1727 Persimmon Dr., Naples, FL (US) 34109

( * ) Notice: Subject to any disclaimer, the term of this patent is extended or adjusted under 35 U.S.C. 154(b) by 0 days.

This patent is subject to a terminal disclaimer.

(21) Appl. No.: 09/440,937

(22) Filed: Nov. 16, 1999

Related U.S. Application Data (63) Continuation-in-part of application No. 09/229,303, filed on Jan. 13, 1999, now Pat. No. 6,149,497.

(51) Int. Cl.[7] .................................................. A41D 27/12
(52) U.S. Cl. ............................... 450/134; 450/155; 2/228
(58) Field of Search .......................... 450/95, 124–126, 450/128, 134, 151, 155; 2/455, 464, 456, 466, 467, 238, 228, 227, 69; 128/96.1, 99.1, 100.1, 101.1, 118.1

(56) References Cited

U.S. PATENT DOCUMENTS

| | | | |
|---|---|---|---|
| 2,493,406 | * 1/1950 | Hicks, III | 450/155 |
| 2,644,449 | * 7/1953 | Champagne | 2/267 |
| 3,071,133 | * 1/1963 | Eisen | 450/155 |
| 4,622,957 | * 11/1986 | Curlee | 602/13 |
| 4,681,113 | * 7/1987 | Coplans | 450/134 |
| 4,993,409 | 2/1991 | Grim . | |
| 5,628,721 | 5/1997 | Arnold et al. . | |
| 5,728,055 | 3/1998 | Sebastian . | |

FOREIGN PATENT DOCUMENTS

| 1 308 535 | 2/1973 | (GB) . |
|---|---|---|
| WO97/42843 | 11/1997 | (WO) . |

* cited by examiner

*Primary Examiner*—Gloria M. Hale
(74) *Attorney, Agent, or Firm*—Heller Ehrman White & McAuliffe LLP (57) ABSTRACT

In order to reduce discomfort induced by menstruation, a panty girdle or the like type of foundation garment is provided with an extensible bladder or a non-extensible element which is arranged to apply pressure to one or both of the sacral or parasacral areas of a female body. In the case of the extensible bladder, the pressure can be varied through the manual manipulation of a squeeze pump that may be built into the waistband of the garment. The garment is additionally provided with an elastic foundation panel that is shaped and designed to reduce bloating and create a trimmer appearance.

9 Claims, 10 Drawing Sheets

FOUNDATION GARMENT FOR THE RELIEF OF MENSTRUAL DISCOMFORT

This application is a continuation-in-part of U.S. patent application Ser. No. 09/229,303, filed Jan. 13, 1999 now U.S. Pat. No. 6,149,497.

BACKGROUND OF THE INVENTION

1. Field of the Invention

The present invention relates generally to a foundation garment. More specifically, this invention relates to a foundation garment that is designed to relieve menstrual discomfort. In addition, the invention relates to a method for alleviating menstrual discomfort using a garment according to the invention.

2. Description of the Related Art

During and shortly prior to menstruation, many women suffer from pain and cramping in the pelvic area. These symptoms occur as a result of congestion in the pelvic area, which distorts the normal anatomy. Because the anatomy is distorted, normal neurovascular function is impaired which in turn contributes to the discomfort.

Although a number of girdle and the like type of garments have been proposed, one which is effective for relieving pain and cramping in the pelvic area prior to and during menstruation has not previously been specifically proposed.

SUMMARY OF THE INVENTION

It is an object of the present invention to provide a foundation garment that is effective for the relief of pre-menstrual and menstrual discomfort.

It is another object of the present invention to provide a foundation garment that applies pressure to the sacral or parasacral areas. It is yet another object of the present invention to provide a foundation garment that conforms to the sacral or parasacral areas. It is still yet another object of the present invention to provide an adjustable pressing force on the sacral or parasacral areas.

It is a further object of the invention to provide a foundation garment, such as a panty girdle or similar type garment, that holds an expansible or non-expansible element against the sacral or parasacral areas of a female body. It is yet a further object of the present invention to direct the force produced by expanding an expansible element against the sacral or parasacral areas of a female body to relieve discomfort incurred as a result of menstruation. It is still yet a further object of the present invention to press a non-expansible element against the sacral or parasacral areas of a female body to relieve discomfort incurred as a result of menstruation.

As it is used herein, the term "expansible element" includes, but is not limited to, a bladder that can be expanded by adding fluid or can be contracted by removing fluid. The term "non-extensible element" includes, but is not limited to, a solid body, a cellular body, or hollow body. Examples of materials that may be used to construct a solid body according to the present invention include organic materials such as feathers, down, or fur, fibrous materials such as wood or paper, reformed metals such as ceramics, metals, natural rubber, natural or synthetic resins, or other polymers. Examples of types of materials that may be used to construct a cellular body according to the present invention include foams, sponge rubber, or other expanded materials. And examples of configurations for hollow bodies according to the present invention include tubes, partial enclosures, and complete enclosures. Of course, other materials and configurations capable of providing a pressing force in accordance with the present invention will become apparent in view of the following disclosure to those skilled in the material arts.

It is an additional object of the invention to provide a fluid bladder that conforms to the epidermal contours over the sacral or parasacral areas of a human female body. It is yet an additional object of the present invention to provide a fluid bladder that applies an adjustable pressing force to the sacral and parasacral areas for reducing pelvic congestion as a result of menstruation and for restoring the normal anatomy.

According to the present invention, these and other objects and advantages of the present invention are also achieved with a foundation garment for providing a therapeutic effect to at least one of the sacral and parasacral regions of a female. The foundation garment comprises a pressing element adapted for conforming to at least one of the sacral and parasacral regions of the female; and a first panel adapted for forcibly applying the pressing element against at least one of the sacral and parasacral regions of the female.

According to the present invention, these and other objects and advantages of the present invention are also achieved with a foundation garment for providing a therapeutic effect to at least one of the sacral and parasacral regions of a female. The foundation garment comprises a bladder adapted for applying a pressing force to at least one of the sacral and parasacral regions of the female; a fluid flow control unit in fluid communication with the bladder for adding fluid to distend the bladder and for removing fluid to collapse the bladder; and a first panel providing a reaction force adapted for directing the pressing force to at least one of the sacral and parasacral regions of the female. The bladder is adapted to be interposed between the first panel and at least one of the sacral and parasacral regions of the female.

According to the present invention, the above and other objects and advantages are also achieved by a method of alleviating menstrual discomfort. The method comprises distending a fluid bladder provided in a foundation garment for producing a pressing force; and directing the pressing force to at least one of a sacral and parasacral region of a humane female body.

These and other objects and advantages of the present invention are set forth in the description that follows, and in part will be readily apparent to those skilled in the art from the description and drawings, or may be learned by practice of the invention. These objects and advantages of the invention may be realized and obtained by means of the instrumentalities and combinations particularly pointed out in the appended claims.

BRIEF DESCRIPTION OF THE DRAWINGS

The present invention will become more clearly appreciated in view of the following description of several preferred embodiments that is made with reference to the appended drawings.

FIG. 6 is a rear elevation view showing the sacral and parasacral areas to which pressure is applied according to the present invention.

DETAILED DESCRIPTION OF THE PREFERRED EMBODIMENT

Figure 1:
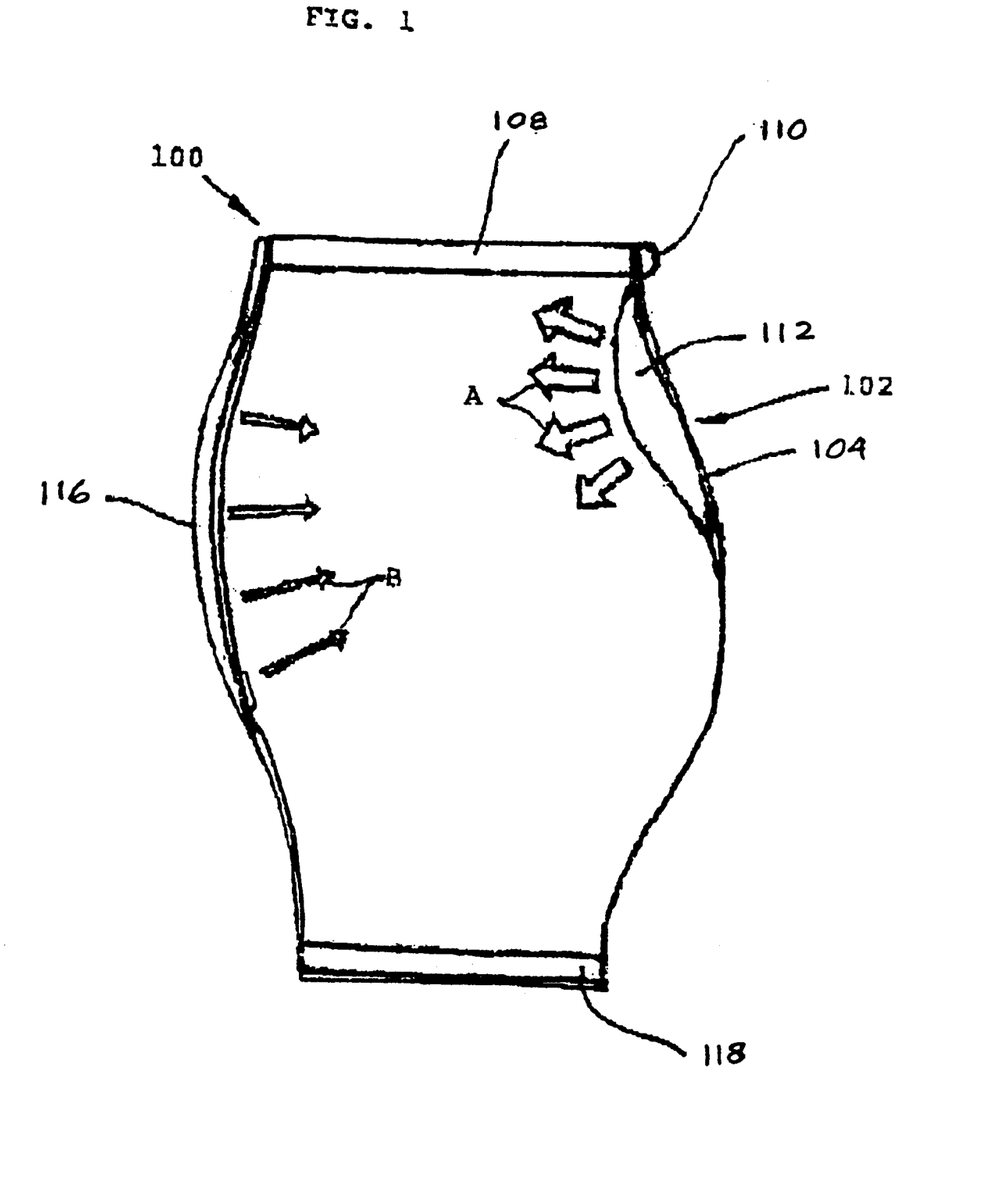
FIG. 1 is a side view of a first preferred embodiment of the invention including an inflatable bladder.
Figure 2:
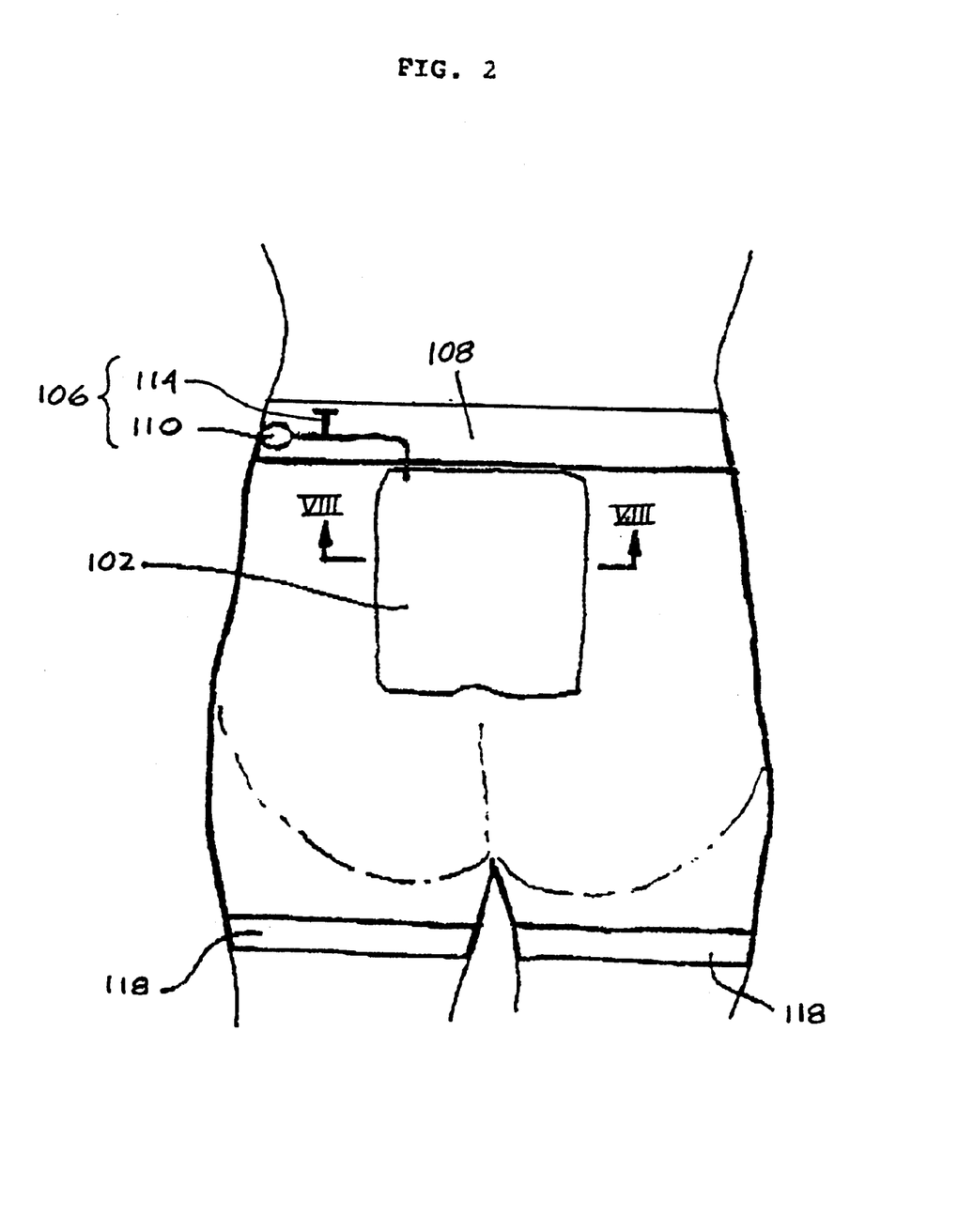
FIG. 2 is a rear elevation view showing a possible configuration of the inflatable bladder shown in FIG. 1.

FIGS. 1 and 2 shows a panty girdle type foundation garment 100 according to a first preferred embodiment of the present invention. The garment 100 includes a distensible pouch or bladder 102 for applying pressure to either or both of the sacral and parasacral areas of a human female's anatomy. The bladder 102 is constructed of a pliable material, such as rubber or suitable synthetic resins, such that the bladder readily conforms to the epidermal contours over the sacral and/or parasacral areas of the female's body.

The bladder 102 is interposed between the female and a panel 104 that is formed of a substantially non-stretchable material, such as nylon. The panel 104 may comprise an integral portion of a homogenous foundation garment, or a separate member securely attached to a conventional foundation garment. The panel 104 may further comprise one or more straps (not shown) for encircling the user's torso to maintain the desired position of the panel 104.

According to a preferred embodiment of the present invention, a fluid flow control unit 106 is positioned in or near a waistband 108 of the garment 100. The fluid flow control unit 106 comprises a fluid supply 110 for adding fluid to a cavity 112 in the bladder 102, and a fluid release 114 for removing fluid from the cavity 112. The fluid supply 110 may comprise a hand-operated pump (e.g., a squeeze bulb), a power operated pump, or a fluid reservoir (e.g., a compressed gas cylinder) for distending the bladder 102. According to a preferred embodiment of the invention, the fluid release 114 comprises a valve for collapsing the bladder 102. The fluid control unit 106 may additionally comprise one or more check valves (not shown) for regulating the direction of fluid flow, a pressure regulator (not shown) for establishing and/or maintaining a desired fluid pressure in the bladder 102, and a collection container (not shown) for holding excess fluid.

The term "fluid," as it is used according to the present invention, comprises any gas, liquid or combination thereof. It is also envisioned that materials capable of transitioning between different states of matter under common ambient conditions may also be used to distend the bladder 102. According to a preferred embodiment of the present invention, the fluid comprises air and/or water.

According to a preferred embodiment of the present invention, an elastic foundation panel 116 is located on the opposite side of the garment 100 with respect to the panel 104, i.e., over the lower abdominal area of a female's body. This panel 116 produces a force "B" in a direction that is designed to reduce bloating and create a trimmer appearance.

Elastic legbands 118 may be provided to prevent the garment 100 from riding up in response to distension of the bladder 102 and/or motion of the user.

Figure 3:
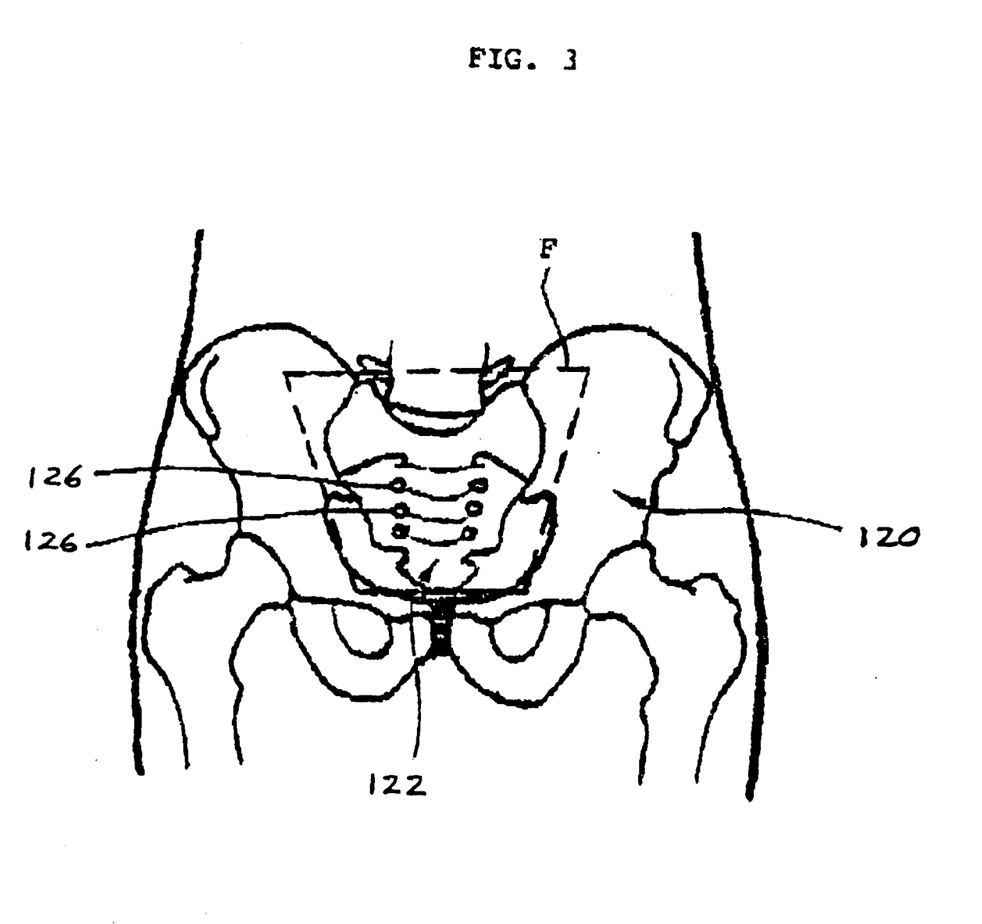
FIG. 3 is a front elevation view showing the area to which pressure is applied by an elastic foundation panel provided at the front of a garment according to the present invention.
Figure 4:
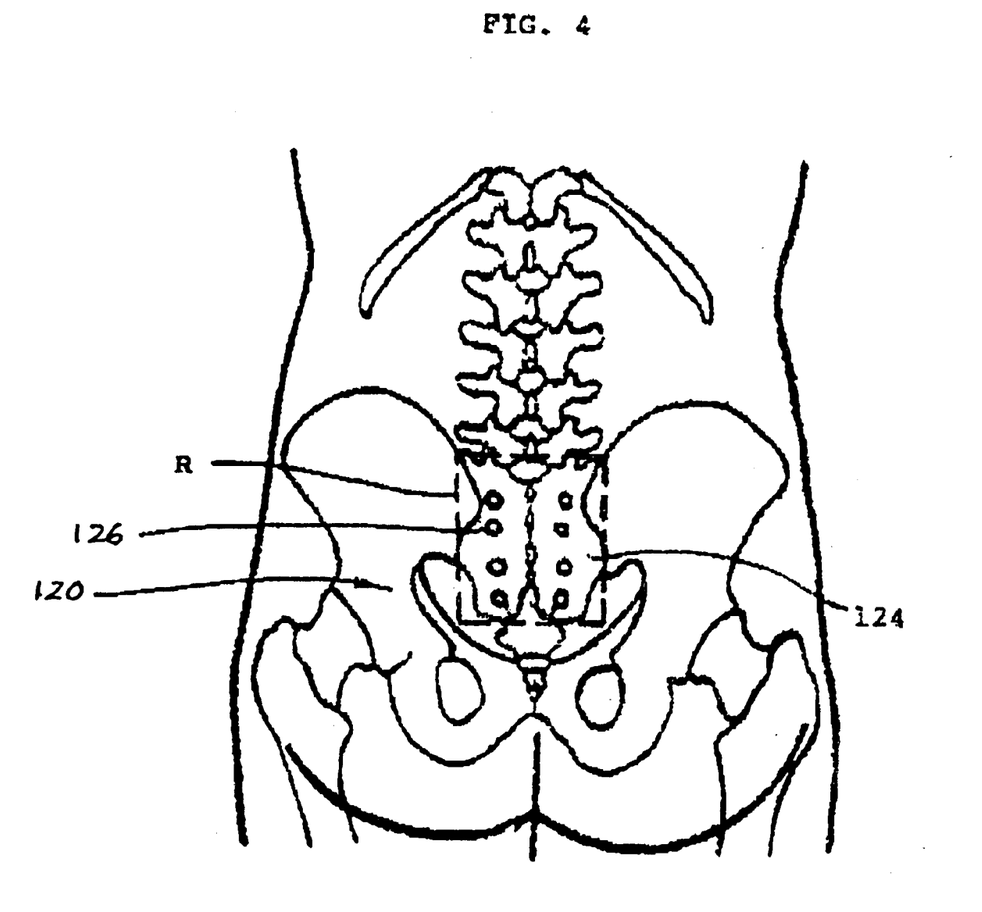
FIG. 4 is a rear elevation view showing the area to which pressure can be applied to the sacral area according to the present invention.

During menstruation the pelvic organs and tissues become engorged with blood, which causes congestion due to edema and swelling of the entire pelvic areas 120 (see FIGS. 3 and 4). This results in pressure being placed posteriorly on the anterior sacrum 122 and sacral area 124. Nerves and veins in the sacral area 124 pass through small holes or sacral foramina 126, and the pressure that is caused by the congestion distorts the normal anatomy and impedes neurologic function and venous drainage. This change in normal venous drainage exasperates the congestion, putting even more pressure on the nerve roots and causing additional discomfort.

The present invention is directed to relieving the congestion and associated discomfort of menstruation by placing pressure on the posterior aspect of the sacrum and parasacral areas 124, 128 (see FIG. 6). The externally applied pressing force "P" (see FIG. 5) helps counteract the pressure that results from vascular tissue engorgement.

Figure 5:
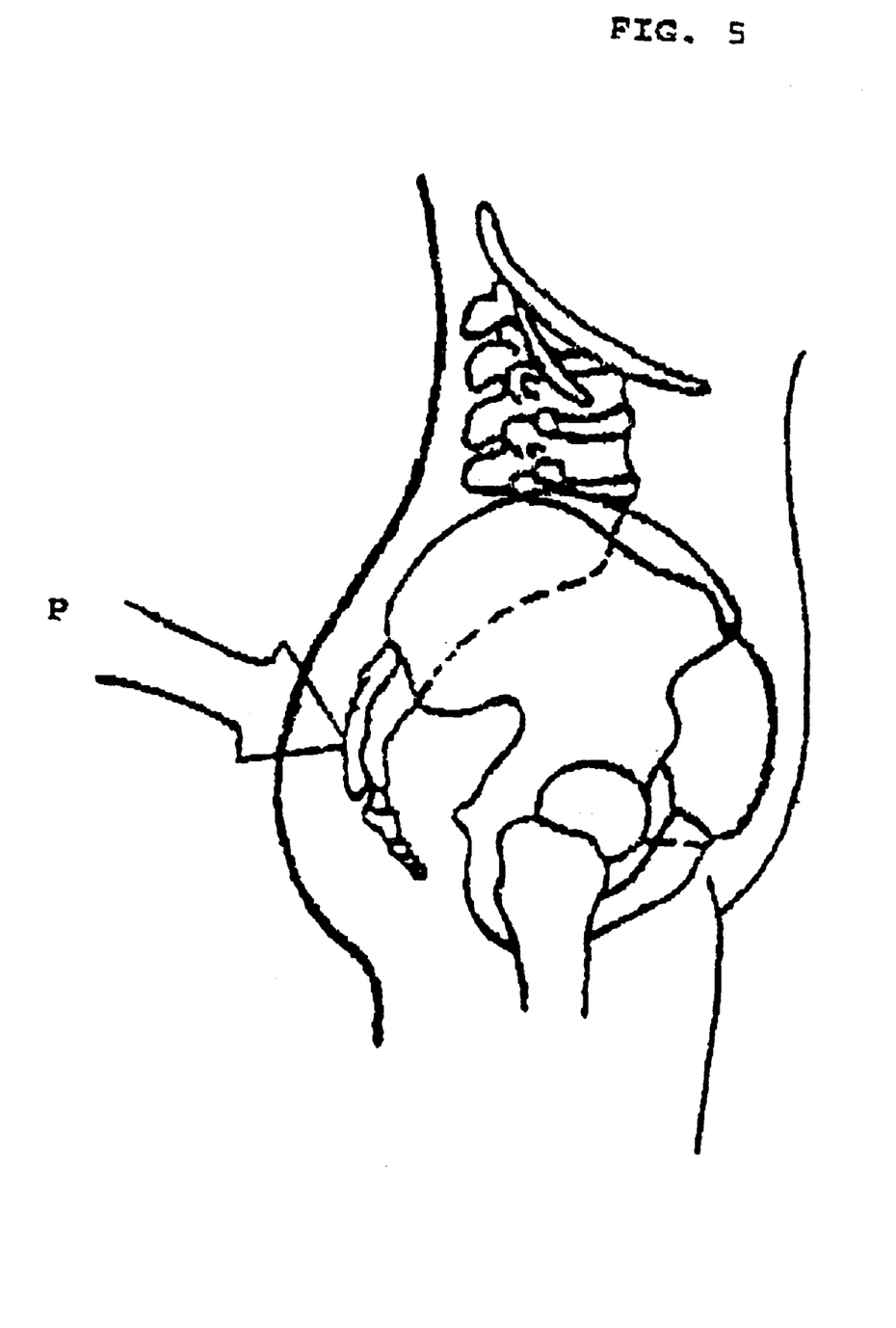
FIG. 5 is a side elevation view showing the direction in which force is applied to the sacral and/or parasacral areas.

According to the present invention, the external pressing force P places the sacrum and parasacral areas 124, 128 in a more normal anatomical relationship, which relaxes the pressure around the sacral foramina 126. This relaxation helps restore normal venous outflow and therefore helps to relieve congestion. Thus, the present invention helps to restore normal anatomy, reduces nerve irritation and decreases pain.

Figure 7:
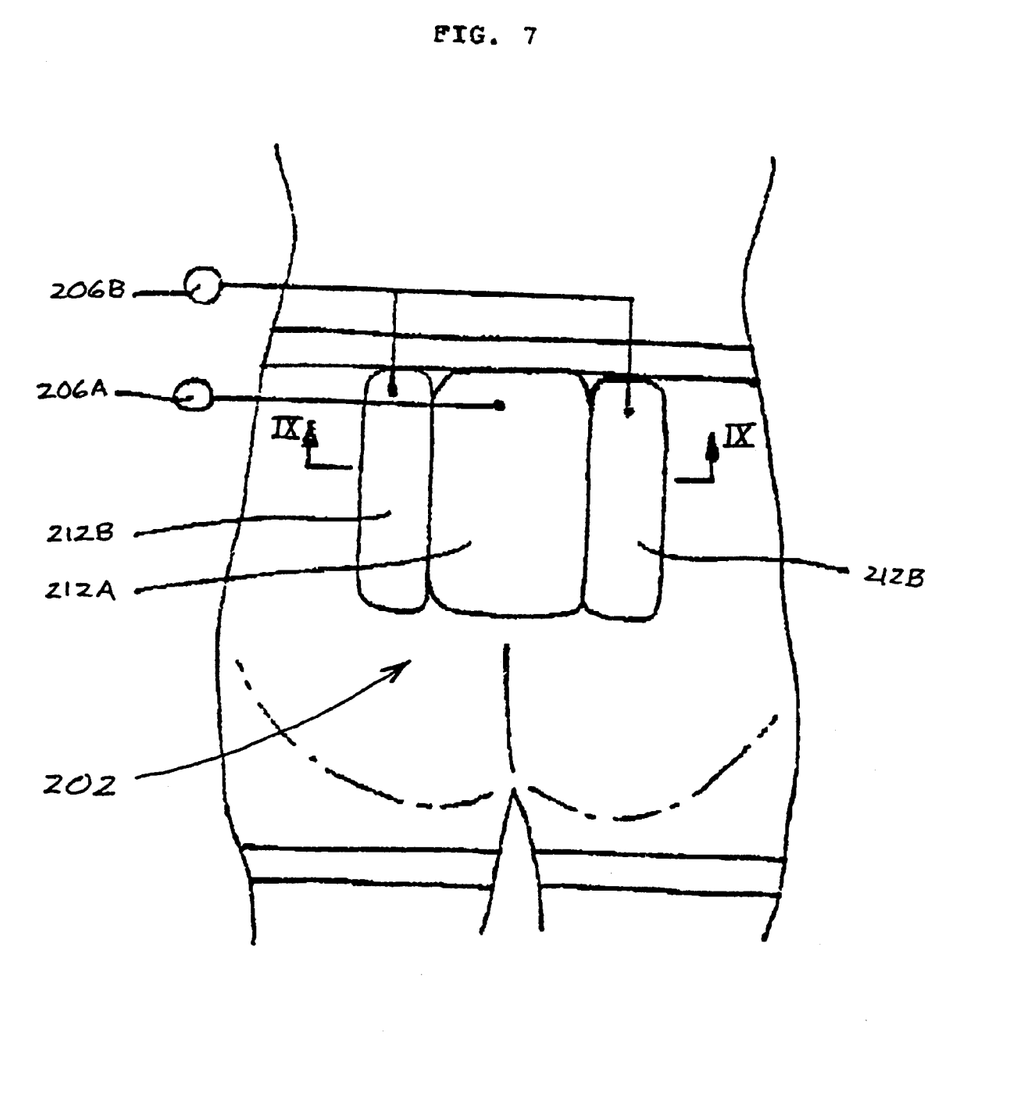
FIG. 7 is a rear elevation view showing a multiple-bladder arrangement according to a second embodiment of the invention.
Figure 9:
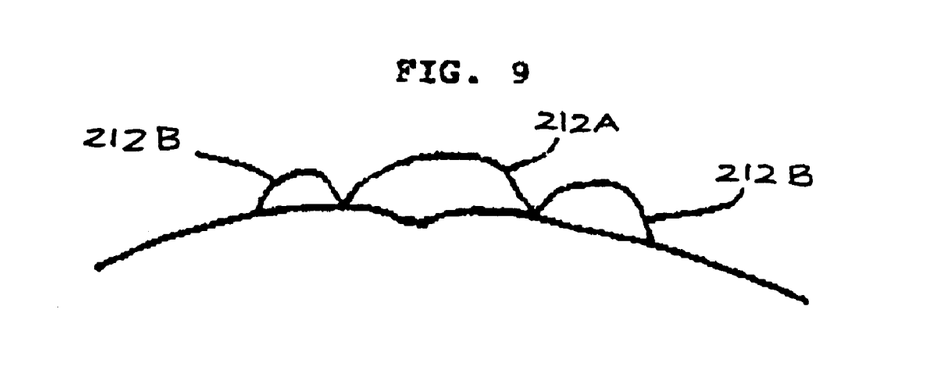
FIG. 9 is a section view taken along section line IX—IX of FIG. 7.

The present invention is not limited to the use of a single cavity bladder. According a preferred embodiment of the present invention, a multiple cavity bladder may enable different pressures to be developed in the different cavities for the comfort of the wearer. FIGS. 7 and 9 show a bladder 202 having separated sacral and parasacral cavities 212A, 212B. Two flow control units 206A and 206B respectively adjust the independent pressures in the cavities 212A, 212B. As shown in FIG. 6, the cavities 212A, 212B may apply different pressing forces to the sacral and parasacral areas 124, 128, respectively. Of course, the flow control units 206A, 206B may be combined in a single unit with appropriate valves for separately adding and removing fluid from each of the cavities 212A, 212B.

Figure 8:
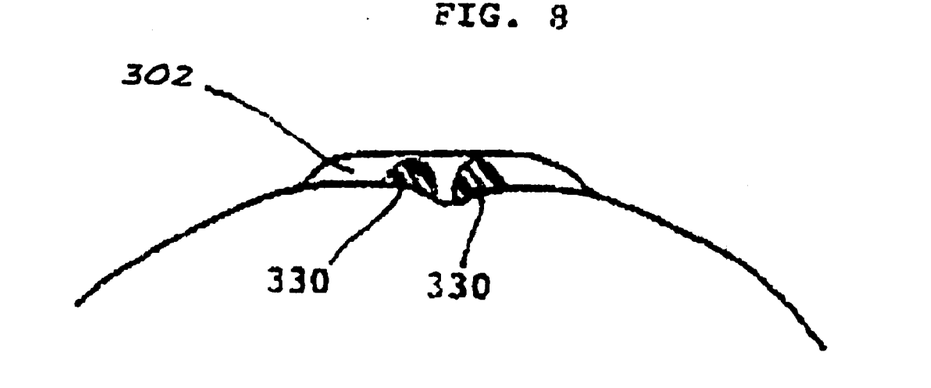
FIG. 8 is a sectional view as taken along section line VIII—VIII of FIG. 2 showing a third embodiment of the present invention wherein foam inserts are included in the bladder.

FIG. 8 shows an arrangement according to a third embodiment of the invention wherein elastomeric or foam inserts 330 are arranged within a bladder 302 to modify the pressing force that is applied the sacral area 124.

Figure 10:
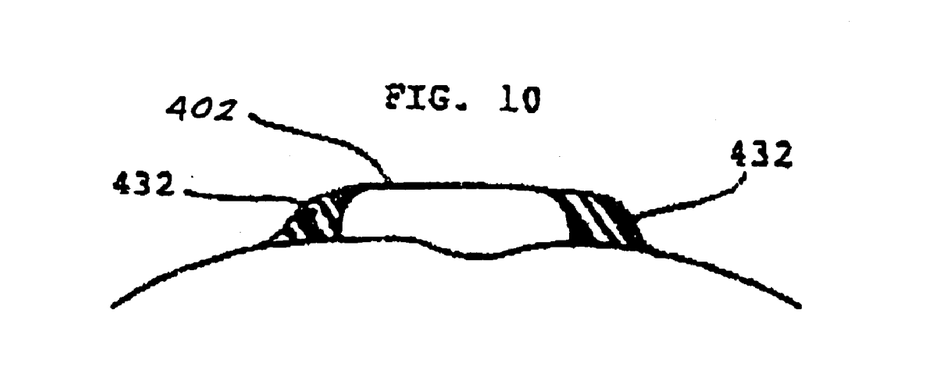
FIG. 10 is a sectional view similar to FIG. 8 showing a fourth embodiment of the present invention wherein the bladder is supplemented with foam.

FIG. 10 shows a fourth embodiment of the invention. In this arrangement, foam pads 432 are located on either side of a bladder 402 in order to modify the pressing force that is applied to the parasacral areas 128.

Figure 11:
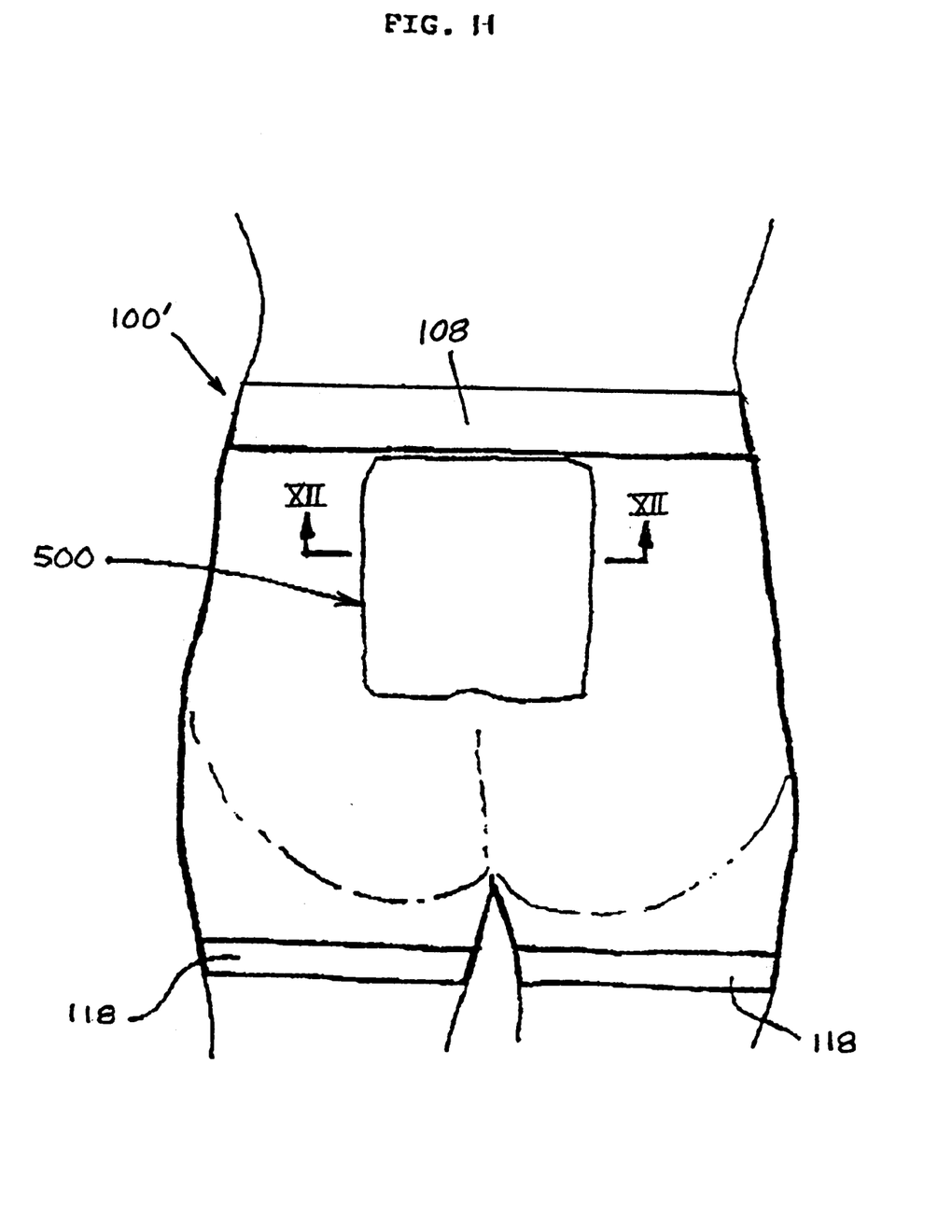
FIG. 11 is a rear elevation view showing an arrangement for a non-extensible element according to the present invention.
Figure 13:
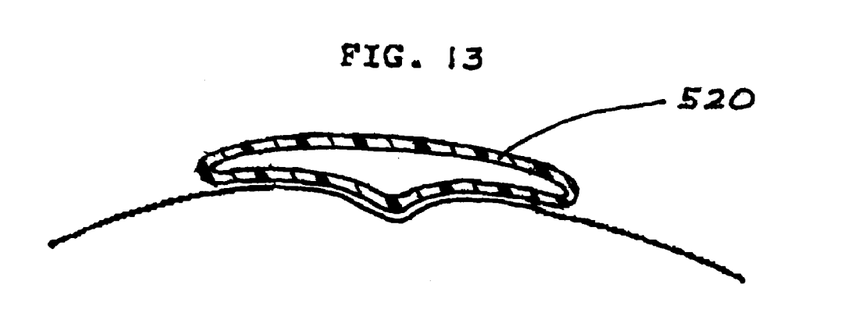
FIG. 13 is a sectional view similar to FIG. 12 showing a sixth embodiment of the present invention wherein the non-extensible element includes a hollow body.
Figure 14:
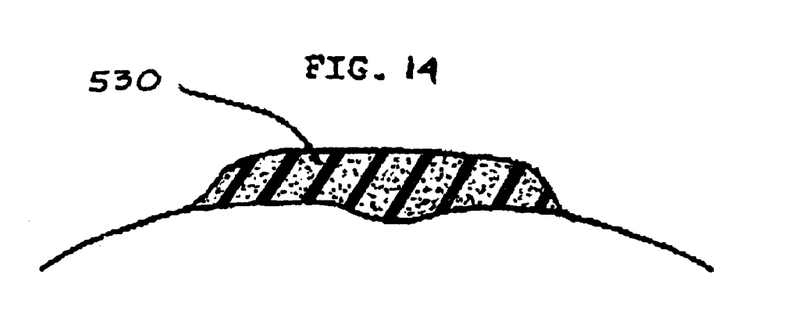
FIG. 14 is a sectional view similar to FIG. 12 showing a seventh embodiment of the present invention wherein the non-extensible element includes a cellular body.

FIG. 11 shows a panty girdle type foundation garment 100' including a non-extensible element 500 according to the present invention. The non-extensible element 500 is positioned for applying pressure to either or both of the sacral and parasacral areas of a human female's anatomy. The non-extensible element may be constructed as a solid body 510 (FIG. 12), a hollow body 520 (FIG. 13), or a cellular body 530 (FIG. 14). In each case, the non-extensible element 500 may be shaped or readily conform to the epidermal contours over the sacral and/or parasacral areas of the female's body.

Like the preferred embodiment described above with respect to FIG. 1, the non-extensible element 500 is interposed between the female and a panel 104 that is formed of a substantially non-stretchable material, such as nylon. The panel 104 may comprise an integral portion of a homogenous foundation garment 100', or a separate member securely attached to a conventional foundation garment 100'. The panel 104 may further comprise one or more straps (not shown) for encircling the user's torso to maintain the desired position of the panel 104.

Also like the preferred embodiment described above with respect to FIG. 1, an elastic foundation panel 116 is located on the opposite side of the garment 100' with respect to the panel 104, i.e., over the lower abdominal area of a female's body. This panel 116 produces a force "B" in a direction that is designed to reduce bloating and create a trimmer appearance. Elastic legbands 118 may also be provided to prevent the garment 100' from riding up in response to motion of the user.

Figure 12:
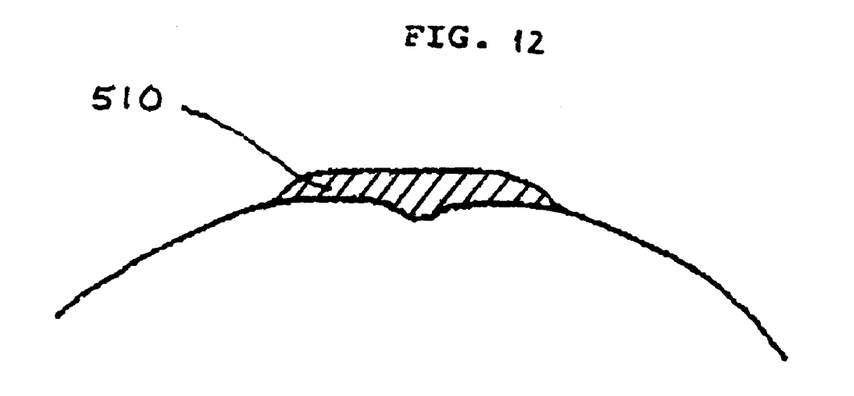
FIG. 12 is a sectional view as taken along section line XII—XII of FIG. 11 showing a fifth embodiment of the present invention wherein the non-extensible element includes a solid body.

Examples of materials that may be used to construct a solid body 510 according to the present invention include organic materials such as feathers, down, or fur, fibrous materials such as wood or paper, reformed metals such as ceramics, metals, natural rubber, natural or synthetic resins, or other polymers. Examples of configurations for hollow bodies 520 according to the present invention include tubes, partial enclosures, and complete enclosures. And examples of types of materials that may be used to construct a cellular body 530 according to the present invention include foams, sponge rubber, or other expanded materials. Of course, other equivalent materials and configurations that are capable of providing the pressing force P in accordance with the present invention will be apparent to those skilled in the art.

Additional advantages and modifications will also readily occur to those skilled in the art. Therefore, the invention in its broader aspects is not limited to the specific details and representative devices, shown and described herein. Accordingly, various modifications may be made without departing from the spirit and scope of the general inventive concept as defined by the appended claims and their equivalents.

I claim:

1. A foundation garment for providing a therapeutic effect to at least one of the sacral and parasacral regions of a female, the foundation garment comprising:

a pressing element adapted for conforming to at least one of the sacral and parasacral regions of the female wherein said pressing element includes an extensible element adapted for applying a pressing force to at least one of the sacral and parasacral regions of the female;

and a first panel adapted for forcibly applying said pressing element against at least one of the sacral and parasacral regions of the female;

wherein the garment directly applies pressure to either or both of the sacral and parasacral areas of the female's anatomy.

2. The foundation garment as set forth in claim 1, wherein said extensible element is adapted for conforming to posterior epidermal contours over at least one of the sacral and parasacral regions of the female.

3. The foundation garment as set forth in claim 1, comprising:

a fluid flow control unit in fluid communication with said extensible element for adding a fluid to distend said extensible element and for removing said fluid to collapse said extensible element.

4. A foundation garment for providing a therapeutic effect to at least one of the sacral and parasacral regions of a female, the foundation garment comprising:

a pressing element adapted for conforming to at least one of the sacral and parasacral regions of the female wherein said pressing element includes a cellular body adapted to conform to at least one of the sacral and parasacral regions of the female;

and a first panel adapted for forcibly applying said pressing element against at least one of the sacral and parasacral regions of the female;

wherein the garment directly applies pressure to either or both of the sacral and parasacral areas of the female's anatomy.

5. The foundation garment according to claim 4, wherein said substantially cellular body is constructed from a material selected from a group consisting of a foam, sponge rubber, and an expanded material.

6. A foundation garment for providing a therapeutic effect to at least one of the sacral and parasacral regions of a female, the foundation garment comprising:

a pressing element adapted for conforming to at least one of the sacral and parasacral regions of the female and wherein said pressing element includes a hollow body adapted to conform to at least one of the sacral and parasacral regions of the female; and a first panel adapted for forcibly applying said pressing element against at least one of the sacral and parasacral regions of the female;

wherein the garment directly applies pressure to either or both of the sacral and parasacral areas of the female's anatomy.

7. The foundation garment according to claim 6, wherein said substantially hollow body has a shape selected from a group consisting of a tube, a partial enclosure, and a complete enclosure.

8. A foundation garment for providing a therapeutic effect to at least one of the sacral and parasacral regions of a female, the foundation garment comprising:

a pressing element adapted for conforming to at least one of the sacral and parasacral regions of the female and wherein said pressing element includes a substantially solid body adapted to be shaped to generally conform to at least one of the sacral and parasacral regions of the female; and a first panel adapted for forcibly applying said pressing element against at least one of the sacral and parasacral regions of the female;

wherein the garment directly applies pressure to either or both of the sacral and parasacral areas of the female's anatomy.

9. The foundation garment according to claim 8, wherein said substantially solid body is constructed from a material selected from a group consisting of wood, metal, natural rubber, natural resin, synthetic resins, and polymers.

* * * * *